United States Patent [19]

Calbo

[11] 4,251,665
[45] Feb. 17, 1981

[54] AROMATIC SULFONIC ACID OXA-AZACYCLOPENTANE ADDUCTS

[75] Inventor: Leonard J. Calbo, Bethel, Conn.

[73] Assignee: King Industries, Inc., Norwalk, Conn.

[21] Appl. No.: 82,050

[22] Filed: Oct. 5, 1979

Related U.S. Application Data

[62] Division of Ser. No. 908,358, May 22, 1978, Pat. No. 4,200,729.

[51] Int. Cl.$^3$ .............................................. C07D 263/52
[52] U.S. Cl. ..................................... 548/215; 548/225; 548/226; 548/227; 548/228; 548/229; 548/232
[58] Field of Search .................. 260/307 FA; 548/215, 548/225, 226, 227, 228, 229, 332

[56] References Cited

U.S. PATENT DOCUMENTS

| | | | |
|---|---|---|---|
| 2,222,506 | 11/1940 | Hodgins et al. | 260/70 |
| 2,226,518 | 12/1940 | Hodgins et al. | 260/70 |
| 2,227,223 | 12/1940 | Hodgins et al. | 260/70 |
| 2,322,979 | 6/1943 | Siegel | 260/70 |
| 2,323,357 | 7/1943 | Rosenblum | 260/29 |
| 2,326,265 | 8/1943 | Tawney | 260/70 |
| 2,327,984 | 8/1943 | West | 260/29 |
| 2,350,894 | 6/1944 | Honel | 260/70 |
| 2,631,138 | 3/1953 | Dannenberg | 260/45.2 |
| 2,764,548 | 9/1956 | King et al. | 252/33 |
| 3,265,645 | 8/1966 | Coney et al. | 260/15 |
| 3,267,174 | 8/1966 | Fry et al. | 260/848 |
| 3,293,324 | 12/1966 | Tropp et al. | 260/850 |
| 3,310,416 | 3/1967 | Schibler | 106/285 |
| 3,474,054 | 10/1969 | White | 260/15 |
| 3,804,920 | 4/1974 | Cunningham et al. | 260/850 |
| 3,957,859 | 5/1976 | Thielcke | 260/505 P |
| 3,960,688 | 6/1976 | Calbo | 204/181 |
| 3,979,478 | 9/1976 | Gallacher | 260/850 |

Primary Examiner—Carman J. Seccuro
Attorney, Agent, or Firm—Morgan, Finnegan, Pine, Foley & Lee

[57] ABSTRACT

Amino resins, e.g., urea-formaldehyde and melamine-formaldehyde thermosetting resin systems, are cured with thermally-decomposable adducts of aromatic sulfonic acids and oxa-azacyclopentanes. The resin products cured with these adducts provide surface coatings having superior water resistance properties. The cured compositions can include other conventional ingredients capable of co-reacting with the amino resins, such as polyols, polyacids, alkyd resins, polyester resins, epoxies, acrylics and the like, to provide compositions curable to products having a wide range of properties.

9 Claims, No Drawings

AROMATIC SULFONIC ACID OXA-AZACYCLOPENTANE ADDUCTS

This is a division of application Ser. No. 908,358, filed May 22, 1978, now U.S. Pat. No. 4,200,729.

This invention relates to superior latent catalysts for curing amino resins. More particularly, it relates to amine adducts of aromatic sulfonic acids for curing coating compositions containing amino resins and other components. Still more particularly, this invention relates to oxa-azacyclopentane adducts of aromatic sulfonic acids for curing urea-formaldehyde and melamine-formaldehyde and similar thermosetting resin systems.

BACKGROUND OF THE INVENTION

Heat-convertible products obtained by reacting amino- or imino-group-containing compounds, e.g., ureas, amides, aminotriazines, and the like, with aldehydes, e.g., formaldehyde, benzaldehyde, etc. have been known for a number of years. Resins obtained by curing such condensation products, e.g., under the influence of heat, possess an excellent combination of physical properties and are widely used in glues, in molding compounds, as finishes for paper and textiles and as surface coatings. The convertible resins can be used per se or they can be further modified before curing, e.g., by alkylation with alcohol, e.g., methanol or butanol, to provide for solubility and compatibility and/or by admixture with other materials capable of co-reacting therewith, such as poly-functional compounds containing hydroxyl groups and carboxyl groups, e.g., glycols, alkyd resins, polyester resins, and the like. This invention broadly is concerned with amino resins which are suitable for all conventional purposes. However, in its most preferred aspects, it is concerned with soluble forms or liquid forms of such amino resin products, which are well known to be superior as coatings for metals, and coatings or impregnants for cloth, paper, and the like. Such convertible resins commonly comprise urea- or melamine-aldehyde condensates or reaction products thereof with alcohols, e.g., methylol ureas, methylol melamines, and alkylated, e.g., methylated and butylated derivatives thereof either alone or in a suitable solvent therefor. These specific amino resins are applied by coating onto three-dimensional substrates, e.g., metal, glass, wood, plastics, such as appliance bodies, plastic windows, and the like, and then curing under the influence of heat. The mechanism of cure contemplated is by condensation and cross-linking to split out $H_2O$ or ROH or HCHO, etc., and curing can be effected without a catalyst if long enough heating times—of the order of hours and days—are provided. However, for immediate curing, or for curing at more moderate temperatures, an acid is often added to function as a cross-linking catalyst. Among the acidic catalysts that have been used in the past with amino resins can be mentioned boric acid, phosphoric acids, acid sulfates, sulfonic and sulfonyl halides, hydrochlorides, ammonium phosphates and polyphosphates, acid salts of hexamethylene tetramine, phthalic acid, oxalic acid, and the like.

In U.S. Pat. No. 3,979,478, assigned to the assignee of this application, it was disclosed that high molecular weight polyalkylaromatic polysulfonic acids, such as dinonylnaphthalene disulfonic acids, are superior catalysts for curing amino resin systems. The patent teaches that these catalysts cure resin systems in short periods of time and produce a resin product having superior physical properties. It was also disclosed that these polyalkylaromatic polysulfonic acids can be stored in the form of thermally-decomposable adducts to provide greater shelf life for the catalyst material. In U.S. Pat. No. 3,474,054, the patentee teaches that amine salts (preferably tertiary amine salts) of aromatic sulfonic acids (e.g., the pyridine salt of para-toluene sulfonic acid) can be utilized to cure amino resin coating compositions. And in U.S. Pat. No. 3,293,324, it is disclosed that the 2-dimethylamino-2-methyl-1-propanol salt of para-toluene sulfonic acid can also be utilized to cure thermosetting aminoplast resins.

It has now been unexpectedly discovered that while certain adducts may be useful for curing amino resin compositions, there are particular adducts which impart outstanding resistance properties to the cured resinous product. Applicant has surprisingly found that aromatic sulfonic acids in association with oxa-azacyclopentanes, such as 4,4-dimethyl-1-oxa-3-aza-cyclopentane, are outstanding latent catalysts for curing amino resin compositions. Moreover, it has been found that these compositions in addition to having superior properties, particularly water resistance properties, in comparison to compositions cured with unneutralized acids, are also superior to other amine adducts of the acids. In addition, the compositions of the invention have exceptional package stability so that they can be stored ready for use for relatively long periods of time without significantly detracting from the usefulness of the compositions.

While it is not clearly understood at this time why the above-described advantageous results are obtained, it is believed that these results may be attributable to a unique combination of the high volatility of the amine component and a low dissociation constant incident to the oxa-azacyclopentane adducts. This combination, in addition to other factors, may provide for a particularly effective association of the adduct with the resin during the curing process to provide for fast curing times and a resin product having superior properties.

DESCRIPTION OF THE INVENTION

According to this invention, in its broadest aspects there are provided compositions which comprise a convertible amino resin and a catalytically effective amount of a thermally-decomposable adduct of an aromatic sulfonic acid and an oxa-azacyclopentane compound.

Preferably, the thermally-decomposable adducts of the invention are of the general formula:

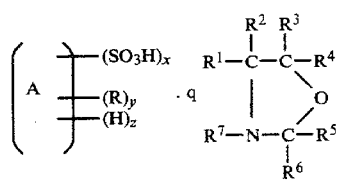

wherein A is phenyl or naphthyl and x is a whole number of from 1 to 8, y is 0 or a whole number of from 1 to the total number of available hydrogens on said phenyl or naphthyl rings, the sum of x and y being no greater than 8, and z is $8-x-y$ when A is naphthyl and $6-x-y$ when A is phenyl; q is a positive number equal to or greater than about 0.5; R is alkyl, halogen, haloalkyl or alkoxy; and $R^1$, $R^2$, $R^3$, $R^4$, $R^5$, $R^6$ and $R^7$, independently, are hydrogen, alkyl, halogen, haloalkyl or alkoxy.

As used herein the term alkyl includes saturated hydrocarbon radicals such as methyl, ethyl, nonyl, didodecyl and the like. The term haloalkyl includes halogenated alkyl radicals such as methyl chloride, ethyl bromide and the like. The term alkoxy includes oxygenated alkyl radicals or epoxies such as methoxy, ethoxy, glycidol derivatives and the like.

The amino resin component can comprise, in general, an amino- or imino-group-containing compound condensed with an aldehyde, dialdehyde or aldehyde precursor. In particular, one can employ a urea-formaldehyde condensate or a triazine-, e.g., melamine-formaldehyde condensate. All such amino resins are obtained in well known manners. Some are materials which are soluble in organic solvents or are capable of being converted to forms, e.g., ether derivatives, which are soluble in such solvents. Amino resin condensates particularly suited for use in the invention include those generally described as alkylated urea-formaldehyde condensates, by which term reference is made to urea-formaldehyde condensates containing subsequently etherified groups derived from alcohols. Urea-formaldehyde condensates are prepared, for example, by reacting formaldehyde with urea in the presence of an acid or alkaline medium so that a methylol urea is formed. This is heat convertible to a cured resin per se. On the other hand, if an alcohol is not present during the initial acid condensation, an alcohol and acid can subsequently be added after initial alkaline condensation. These latter procedures are suitable to alkylated urea-formaldehyde condensates derived from saturated aliphatic alcohols of 2 to 8 carbon atoms, and particularly suitable for impregnation or use in combination with other co-reactants are urea-formaldehyde condensates obtained from methanol or n-butyl alcohol. These alkylated urea-formaldehyde condensates are soluble in H₂O, sometimes, and many solvents including hydrocarbons, ketones, esters and alcohols. Preparation of the condensates will not be reiterated here in detail since they have been repeatedly described in the prior art and the preparation is adequately disclosed in U.S. Pat. Nos. 2,222,506; 2,226,518; 2,227,223; 2,322,979; 2,327,984; 2,323,357; 2,326,265 and 2,350,894.

The triazine-aldehyde condensation products are also made in known ways. Any triazine having two or more amino groups can be reacted with any aldehyde, preferably in the presence of a mild alkaline catalyst in aqueous or non-aqueous media. They can also be reacted in a solvent, such as n-butanol, which produces an alkylated derivative. An excess of formaldehyde per mole of amino group is used. Among the amino triazines there can be used melamine, ammeline, 2-chloro-4,6-diamino-1,3,5-triazine, 2,4-diamine triazine, N,N-dimethyl melamine, benzoguanamine, acetoguanamine and the like. The aldehyde component can comprise paraformaldehyde, acetaldehyde, glyoxal, paraldehyde, benzaldehyde, furfural, and the like. The solvent, if used, can vary widely and can include inert solvents, preferably those easily volatized, such as toluene, xylene, benzene, and the like, or, as mentioned, the solvent can be reactive with the condensation product, in the sense of producing alkylated products such as methanol, butanol, or the like. Water can also be used as a solvent for some of the low molecular weight resins which are sometimes referred to as cross-linking resins.

As with urea resins, the triazine-based amino resins can be reactive products of the aldehyde and the triazine or can be modified, e.g., by reaction with an alcohol in an acidic medium, such as methanol or n-butanol to form the corresponding ethers, which are also heat convertible and somewhat more compatible with solvents and co-reactants. All such compositions can be made by those skilled in the art and many of them are commercially available, from a number of sources.

All of the amino resins can be modified with conventional amounts of conventional modifiers, such as polyols, acetates, alkyd resins, other resins, and the like. These add flexibility, different surface appearance, and modify resistance to chemicals, weathering, and the like, as is well known.

The curing of the present invention is effected by admixing the aromatic sulfonic acid oxa-azacyclopentane adduct with the above-described amino resin compositions. The adduct can be used per se or it can be diluted in a solvent such as isopropanol or 2-ethoxyethanol. Upon heating the mixture to the curing temperature, the adduct breaks down into the sulfonic acid form and the volatile amine, whereupon the sulfonic acid serves to catalyze the curing reaction. The cure is especially rapid at elevated temperatures, e.g., from about 1 minute at 200° C. to about 1 hour at 80° C.

The aromatic sulfonic acid component of the adduct can vary widely in chemical nature. These acids can have a single aromatic ring, such as the benzene derivatives, or they can have a diaromatic ring, such as the naphthalene compounds. One sulfonic acid substituent can be used or, a plurality of such acid substituents can be employed. When the acid has a single aromatic ring, the acid is of the alkyl-benzene sulfonic acid type wherein the alkyl substituents can be positioned on the aromatic ring in either the ortho, meta or para position from the sulfonic acid substituent. Preferably, when an acid having a single aromatic ring is employed the alkyl group is positioned on the aromatic ring in the para position with respect to the sulfonic acid group. Among the alkyl-benzene sulfonic acids that can be employed for use in the invention are, e.g., the para-decyl benzene sulfonic acids, the para-dodecyl benzene sulfonic acids and the like. The preferred alkyl-benzene sulfonic acid is para-toluene sulfonic acid.

As indicated above, instead of a single aromatic nucleus, the acids can have a naphthalenic structure. Many variations on the positions of substituents of these naphthalenic structures are also possible and contemplated and mixed positional isomers are also included. The naphthalenic acids can also have either one, or more than one, sulfonic acid substituent as well as alkyl substituents, which can be straight or branched chain. Among the naphthalenic type aromatic sulfonic acids that can be employed are the dihexyl naphthalene disulfonic acids, the diheptyl naphthalene disulfonic acids, the dihexyl naphthalene sulfonic acids and the like.

The most preferred sulfonic acid components of the adducts of the invention are the branched alkyl substituted naphthalene polysulfonic acids described in Gallacher, U.S. Pat. No. 3,979,478, assigned to the assignee of this application and incorporated herein by reference. These acids have a molecular weight of at least about 500 and have at least two alkyl groups and two sulfonic acid groups on the naphthalenic nucleus. The alkyl substituents can be straight or branched chain. Best results are obtained with maximum variations in substituent locations and maximum branching. These naphthalenic acids are available for example, by sulfonating polyalkylnaphthalenes. The polyalkylnaphthalenes can be made by alkylating naphthalene with olefins, for example, propylene trimer or tetramer, or alkyl halides, with a suitable catalyst, e.g., hydrogen fluoride or anhydrous aluminum chloride in a suitable solvent such as naphtha, sulfur dioxide, nitrobenzene or a mixture of benzene and nitrobenzene. See Robert G. King and George W. Thielcke, U.S. Pat. No. 2,764,548, also assigned to the assignee of the present invention. Such a process produces naphthalene substituted with alkyl groups and, if a branched olefin is used, such as propylene trimer or propylene tetramer,—obtained by polymerizing propylene by an acid catalyst such as phosphoric acid, then the alkyl groups will be highly branched as well. Sulfonation is obtained by treating the polyalkylaromatic with a sulfonating agent. For example, the dialkylaromatic compound is dissolved in an inert solvent, such as petroleum naphtha, hexane, heptane, octane, chlorinated solvents, and the like, and sulfuric acid, preferably oleum, is introduced into the solution at the desired temperature and with agitation. After reaction is complete, the polysulfonic acid—and also some monosulfonic acid—is recovered by adding water to selectively extract the polysulfonic acid, then extracting the polysulfonic acid from the water, e.g., by extraction with a water immiscible solvent such as pentanol, hexanol, heptanol, octanol, decanol, and the like. A detailed technique for preparing dinonylnaphthalene disulfonic acid, didodecylnaphthalene disulfonic acid and isomers and analogs thereof, including the benzene analogs, is described in the King et al patent, U.S. Pat. No. 2,764,543. A preferred, optional isolation procedure is described in the commonly assigned Thielcke patent, U.S. Pat. No. 3,957,859, incorporated herein by reference to save unnecessarily detailed disclosure.

The oxa-azacyclopentane components of the adducts of the present invention include a broad range of compounds having the general formula:

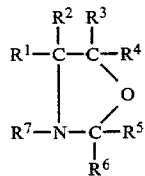

wherein $R^1$, $R^2$, $R^3$, $R^4$, $R^5$, $R^6$ and $R^7$, independently, are hydrogen, alkyl, halogen, haloalkyl or alkoxy.

These compounds can vary widely in chemical nature so long as both nitrogen and oxygen are included in the cyclopentane ring. The alkyl substituents can be straight or branched chain. Best results are obtained when the alkyl substituents are short chain alkanes.

The most preferred oxa-azacyclopentane is 4,4-dimethyl-1-oxa-3-aza-cyclopentane, known in the art as oxazolidine. This compound can be prepared by reacting the composition 2-amino-2-methyl propanol with formaldehyde. The reaction product of these reactants is then dehydrated in a slightly acidic medium to form the oxazolidine product. A review of oxazolidine chemistry is found in the publication *Chemical Reviews*, E. D. Bergmann, Vol. 53, pp. 309–352 (1953), which disclosure is incorporated herein by reference.

As indicated above, the latent catalysts of the present invention are adducts of aromatic sulfonic acids and oxa-azacyclopentane compounds. These compounds can unite as adducts in a wide range of molar ratios, depending on the particular materials employed and the properties of the components added. For example, the molar ratio of aromatic sulfonic acid groups to oxa-azacyclopentane compound suitable for use in the adducts of the invention can range from 1:0.5 to about 1:2.5. The most preferred molar ratio of aromatic sulfonic acid groups to oxa-azacyclopentane compound is about 1:1 for each sulfonic acid group present.

The procedures for preparing the adducts are well known to those skilled in the art and involve treating the aromatic sulfonic acid with oxa-azacyclopentane to effect neutralization of the acid. The acid can be used per se or it can be diluted in a solvent such as isopropanol or isobutanol. Oxa-azacyclopentane is added to the acid, either alone or in a solvent such as isopropanol or water, in an amount sufficient to raise the pH of a 1:1 mixture of the latent catalyst solution with water to about 4 to 8. The preferred pH range is 7.2 to 7.5. The resulting solution may be hazy and normal separation techniques such as filtration can be employed to purify the latent catalyst product.

It is preferred to employ such a proportion of the latent catalyst that the cured amino resin compositions contain about 0.1 to 12% of the aromatic sulfonic acid component based on the weight of binder solids. When about 0.1 to 12% of aromatic sulfonic acid component is employed, the resulting cured resinous product exhibits outstanding water resistance properties such as the resistance to rusting. The cured product is also hard, tough, has excellent adhesion to substrates and excellent resistance to the deteriorating and destructive action of heat and chemicals, particularly alkalies. The cured resinous products produced from the compositions of the invention are thus of great value as surface coating films and impregnants for materials which come into repeated contact with water and alkalies, such as soapy water. Thus, the compositions of the invention can be used as surface coatings for washing machines and in making heat resistant paper based laminates, e.g., for bar- and countertops. A more preferred range of latent catalyst concentration is from about 0.2 to 6%.

Although not essential, it is generally preferred to effect the mixing of the latent catalyst with the amino resin condensate and, if used, a co-reactant, all in water or a solvent. The urea and melamine condensates as well as glycol, polyether, alkyd resin and other co-reactive additives are soluble in a variety of solvents including ketones, such as acetone, methyl ethyl ketone, methyl isobutyl ketone, isophorone, etc.; esters, such as ethyl acetate, butyl acetate, ethylene glycol mono ethyl ether acetate, such as 2-ethoxyethanol acetate, etc.; and ether alcohols, such as methyl, ethyl or butyl ether of ethylene glycol or diethylene glycol. Alcohols such as ethanol, isopropanol, n-butanol, etc. are also used by themselves in some cases. To save expenses, the most efficient, non-alcoholic solvents are ordinarily used in admixture with diluents which are themselves not universal solvents when used alone, but which may not be incorporated with active solvents. Reference is made in this respect to aromatic hydrocarbons, such as benzene, toluene, xylene, aromatic petroleum thinner, etc.; and alcohols recited above. For use in coatings and impregnants, in order to achieve desired evaporation and drying characteristics, the solvents used with the present compositions are combined and balanced for desired properties in the manner well known in the lacquer, varnish and laminating arts. It is also often convenient to add the aromatic sulfonic acid.oxa-azacyclopentane adduct as a solution in an organic solvent such as glycol ethers like 2-ethoxyethanol; alcohols such as ethanol, isopropanol and n-butanol; or ketones such as acetone or methyl ethyl ketone, as well as mixtures of two or more of such liquid compounds. Isopropanol is especially convenient.

Conventionally, the amino resins, the aromatic sulfonic acid.oxa-azacyclopentane adduct and if present, co-reactants, may contain various other materials such as pigments, colorants, surfactants, fillers, and the like. Pigments such as titanium dioxide, antimony oxide, lead oxide, carbon black, chrome yellow, zinc oxide, para red, and the like, can be used in the compositions. Best results in preparing enamels are obtained by grinding the pigment with a portion of the solvent and amino resin and then adding the remainder of the solvent and, e.g., a glycol, an alkyd resin, other polyester resins, etc. after the grinding operation. The enamel is ready for application after addition of the desired amount of the adduct.

When varnishes, lacquers or enamels are prepared from the composition of this invention, layers of suitable thickness of the film-forming material may be applied to a surface such as metal, wood, or the like. Curing completely therethrough is attained because the conversion to an insoluble film is not dependent upon contact with air. This fact also makes the compositions valuable in manufacture of laminates wherein the laminae are cloth, paper, glass-coth, and the like. Such laminae are impregnated with a solution of the amino resin and curing catalyst, optionally with co-reactants. After drying, the impregnated sheets are stacked and cure is effected in a heated press.

Many of the catalyzed amino resin compositions are also suitable for molding operations wherein they are introduced into a mold, compressed and the cure completed with heat. Various fillers, dyes and pigments may be incorporated with the compositions in use for molding operations such as wood flour, talc, alpha-cellulose, zinc sulfide, etc. All such techniques are well known to those skilled in this art.

DESCRIPTION OF THE PREFERRED EMBODIMENTS

The following examples illustrate compositions within the scope of the present invention. They are not to be construed as being limiting in any manner whatsoever. All parts are by weight.

EXAMPLE 1

Preparation of the Latent Catalyst 1 kilogram of a 54% solution of dinonylnaphthalene disulfonic acid (1.0 mol.) in isobutanol is charged to a suitable reaction vessel equipped with stirrer. To it is added with stirring 938 grams of isopropanol, followed by the slow addition of 223 grams (2.2 mol.) of 4,4-dimethyl-1-oxa-3-azacyclopentane (oxazolidine). The resulting solution is 25% active as dinonylnaphthalene disulfonic acid. If the solution appears hazy and if deemed necessary, it can be filtered. The pH of the mixture at a 1:1 dilution of the latent catalyst solution with water should be approximately 7.0–7.5.

EXAMPLE 2

Compositions cured with catalyst systems of (A) the dinonylnaphthalene disulfonic acid.oxazolidine adduct of the present invention, (B) dinonylnaphthalene disulfonic acid and (C) dinonylnaphthalene disulfonic acid.-Triisopropanolamine adduct are compared. An amino resin stock solution is prepared by adding 25 grams of isopropanol to 75 grams of LTX-125 with stirring. (LTX-125 refers to a 95% solids alkylated melamine-formaldehyde resin manufactured by the Monsanto Co.)

SOLUTION A

The dinonylnaphthalene disulfonic acid.oxazolidine system of the present invention is prepared by adding 2.10 grams of the latent catalyst prepared in accordance with Example 1 to 40 grams of the stock solution.

SOLUTION B

For comparison purposes, another solution is prepared by adding 0.9 grams of a 53.5% solution of dinonylnaphthalene disulfonic acid to 40 grams of the stock solution.

SOLUTION C

As a second comparison, a solution is prepared in the same fashion as SOLUTION A by adding 2.58 grams of a triisopropanolamine adduct of dinonylnaphthalene disulfonic acid to 40 grams of the stock solution.

SOLUTIONS A, B and C are separately cast on untreated steel with a 1.0 mil. wire wound rod and cured for 30 minutes at 220° F. The three solutions are evaluated for surface properties in accordance with the pencil hardness test (ASTM test method No. D-3383-75), the Double MEK Rubs Test and an elevated temperature water soak test wherein the coatings are treated for 1 hour at 50° C. The Double MEK Rubs test comprises saturating a cloth with methyl ethyl ketone solution and rubbing the film to be tested back and forth in double rub fashion until the underlying panel becomes visible. The results of these tests are tabulated below:

| Solution | Catalyst System | Film Thickness | Pencil Hardness | Double MEK Rubs | 1 hr. 50° C. Water Soak |
|---|---|---|---|---|---|
| B* | DNNDSA | 0.6 | H/2H | 100 | No attack |
| A | DNNDSA . Oxazolidine | 0.6 | H/2H | 100 | No attack |
| C* | DNNDSA . Triisopropanolamine | 0.6 | Tacky - not cured | | |

*For comparative purposes

EXAMPLE 3

25 grams of isopropanol is added with stirring to seventy-five grams of LTX-125 resin to form a stock solution. The composition of LTX-125 resin is described in Example 2. For comparison purposes, dinonylnaphthalene disulfonic acid and several amine adducts thereof, including the oxazolidine adduct of the present invention, are added to aliquots of the LTX-125 stock solution. In all cases the amount of dinonylnaphthalene disulfonic acid is kept constant at 1.6% based on the weight of binder solids and the pH of the catalyst solutions are adjusted to a range of 7.2 to 7.5. The blends prepared for comparison are separately cast on untreated steel with 1.0 mil. wire wound rod and baked for 30 minutes at 200° F. with the following results:

| Catalyst System | Pencil Hardness | Double MEK Rubs | 50° C. Water Soak 1 hr. | 3 hr. |
|---|---|---|---|---|
| *DNNDSA | H/2H | 100 | No rust | Light rust |
| DNNDSA . Oxazolidine adduct | H/2H | 65 | No rust | Light rust |
| *DNNDSA . Ammonium adduct | H/2H | 45 | No rust | Heavy rust |
| *DNNDSA . Dimethyl ethanol-ammonium adduct | H/2H | 20 | Rusted | — |
| *DNNDSA . Diethyl ethanol-ammonium adduct | 2B/B | 5 | Rusted | — |

*For comparative purposes

The data from the pencil hardness, double MEK rubs and water soak tests in Examples 2 and 3 demonstrate that the aromatic sulfonic acid.oxazolidine latent catalysts of the present invention provide fast cure response for amino resin compositions and, in addition, produce resin products having superior water resistance properties compared to other amine adducts of aromatic sulfonic acids.

EXAMPLE 4

The latent catalyst system of the present invention is compared to an unneutralized acid system.

A master batch of the following weight proportions is prepared:

|  | Parts |
|---|---|
| Acryloid OL-42 | 360 |
| Cymel 303 | 155 |
| FC-430 surfactant | 1.7 |
| 2-ethoxyethyl acetate | 14 |
| Butyl acetate | 30 |
| 2-ethoxyethanol | 74 |
|  | 634.7 |

Acryloid OL-b 42 is a hydroxyl-functional type thermosetting acrylic resin manufactured at 80% solids in 2-ethoxyethyl acetate by the Rohm and Haas Company, Philadelphia, Pa. Cymel 303 is a liquid hexamethoxymethylmelamine composition manufactured by the American Cyanamid Company. FC-430 surfactant is a fluorocarbon manufactured by the 3M Company.

To 100 parts of the master batch solution is added 2.1 parts of a 53.5% solution of dinonylnaphthalene disulfonic acid (DNNDSA). As a comparison, a second coating mixture is formulated by adding 4.48 grams of the oxazolidine adduct of DNNDSA. Both coating mixtures contain 1.6% of dinonylnaphthalene disulfonic acid based on the weight of binder solids. Films of the two solutions are separately cast on an untreated steel substrate and cured to a dry film thickness of 1.1 mil. In a first test, the coatings are cured at a temperature of 200° F. for 30 minutes. In a second test, other samples of the two coatings are cured at a temperature of 250° F. for 30 minutes. The results are tabulated below:

| Cure Temp. 30' at 200° F. | Pencil Hardness | Double MEK Rubs | 1 hr. 50° C. Water Soak |
|---|---|---|---|
| *DNNDSA | 2B/B | 28 | Heavy rusting |
| DNNDSA . Oxazolidine adduct | 2B/B | 20 | No attack |

| Cure Temp. 30' at 250° F. | Hardness | MEK Rubs | Appearance | Pencil Hardness |
|---|---|---|---|---|
| *DNNDSA | F/H | 200 | Medium rust | B/HB |
| DNNDSA . Oxazolidine adduct | F/H | 180 | Very light rust | B/HB |

*For comparative purposes

The data from the pencil hardness, double MEK rubs and water soak tests in Example 4 demonstrate that resins prepared from the aromatic sulfonic acid.oxazolidine adducts of the present invention possess superior water resistance properties than resins cured from the unneutralized acid.

EXAMPLE 5

Preparation of Latent Catalysts

Oxazolidine salts of (1) dinonylnaphthalene disulfonic acid, (2) para-toluene sulfonic acid and (3) dinonylnaphthalene sulfonic acid (mono acid) are prepared by the same procedure described in Example 1. The pH of each mixture is adjusted to 7.0 to 7.5 by the slow addition of 4,4-dimethyl-1-oxa-3-azacyclopentane. The solutions are then finally adjusted, if necessary, to 25% active sulfonic acid solids by the addition of isopropanol.

EXAMPLE 6

The compositions cured with three oxazolidine adducts of the invention prepared in accordance with Example 5 are compared with three compositions cured with acids which have not been neutralized.

An amino resin stock solution is prepared by diluting 300 grams of LTX-125 with 100 grams of isopropanol.

The six solutions are prepared as follows:

SOLUTION A

A dinonylnaphthalene disulfonic acid.oxazolidine system is prepared by adding 3.8 grams of the latent catalyst prepared in accordance with Example 5 (salt number 1) to 80 grams of the stock solution.

SOLUTION B

A para-toluene sulfonic acid.oxazolidine system is prepared by adding 2.4 grams of the latent catalyst prepared in accordance with Example 5 (salt number 2) to 80 grams of the stock solution.

SOLUTION C

A dinonylnaphthalene sulfonic acid.oxazolidine system is prepared by adding 6.75 grams of the latent catalyst prepared in accordance with Example 5 (salt number 3) to 80 grams of the stock solution.

SOLUTION D

For comparison purposes, a solution is prepared by adding 1.75 grams of dinonylnaphthalene disulfonic acid solution of Acid Number 110 to 80 grams of the stock solution.

SOLUTION E

As a second comparison, another solution is prepared by adding 1.75 grams of para-toluene sulfonic acid solution of Acid Number 110 to 80 grams of the stock solution.

SOLUTION F

As a third comparison, a solution is prepared by adding 3.91 grams of dinonylnaphthalene sulfonic solution of Acid Number 49 to 80 grams of the stock solution.

SOLUTIONS A-F all contain the same number of acid equivalents. The six solutions are separately cast on untreated steel panels with a 1.0 mil. wire wound rod and cured for 30 minutes at 200° F. The six solutions are evaluated for surface properties in accordance with the pencil hardness test, the double MEK rubs test and the elevated temperature water resistance soak test. The results are tabulated below:

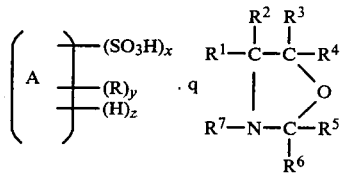

| | | Tabulated Results of Example 6 | | | | | |
|---|---|---|---|---|---|---|---|
| | | Film | Pencil | Double | | Water Soak, 50° C. | |
| Solution | Catalyst System | Thickness | Hardness | MEK Rubs | 1 hr. | 3 hr. | 6 hr. |
| A | DNNDSA . Oxazolidine | 0.55 | 2/3H | 100 | NA | NA | NA |
| *D | DNNDSA | 0.55 | 2/3H | 100 | NA | very light rust | light rust |
| B | TSA . Oxazolidine | 0.55 | 2/3H | 100 | NA | very light rust | very light rust** |
| *E | TSA | 0.55 | 2/3H | 100 | med. rust | med. rust | heavy rust** |
| C | DNNSA . Oxazolidine | 0.55 | H/2H | 100 | NA | NA | very light rust |
| *F | DNNSA | 0.55 | 2/3H | 100 | very light rust | very light rust | med. rust** |

NA = No ATTACK
*For comparative purposes
**Edge lifting

The data from the tests in Example 6 demonstrate that the aromatic sulfonic acid.oxazolidine latent catalysts of the present invention provide fast cure response for amino compositions and, in addition, produce resin products having superior water resistance properties and edge lifting properties compared to the unneutralized acids. These tests also show that the water resistance of the disulfonic acid adduct is greater than that of the mono sulfonic acid adduct and the toluene sulfonic acid adduct. The tests further show that the adhesion of the film to the substrate is better for the dinonylnaphthalene disulfonic acid adduct than for the mono sulfonic acid adduct and the toluene sulfonic acid adduct.

All obvious modification and variations which will suggest themselves to those skilled in the art in the light of the above detailed description are included within the scope of the present invention. The invention is to be defined by the appended claims.

I claim:

1. A thermally-decomposable composition comprising an oxa-azacyclopentane adduct of an aromatic sulfonic acid of the general formula:

$$\left( A \begin{array}{c} -(SO_3H)_x \\ -(R)_y \\ -(H)_z \end{array} \right) \cdot q \quad \begin{array}{c} R^2 \; R^3 \\ | \; | \\ R^1-C-C-R^4 \\ | \quad \quad \backslash \\ | \quad \quad \; O \\ | \quad \; \; / \\ R^7-N-C-R^5 \\ | \\ R^6 \end{array}$$

wherein A is phenyl or naphthyl and x is a whole number of from 1 to 8, y is a whole number of from 0 to 7, the sum of x and y being no greater than 8, and z is $8-x-y$ when A is naphthyl and $6-x-y$ when A is phenyl; q is a positive number equal to or greater than about 0.5; R is alkyl, halogen, haloalkyl or alkoxy; and $R^1$, $R^2$, $R^3$, $R^4$, $R^5$, $R^6$ and $R^7$, independently, are hydrogen, alkyl, halogen, haloalkyl or alkoxy.

2. A composition as defined in claim 1 wherein said composition is of the formula:

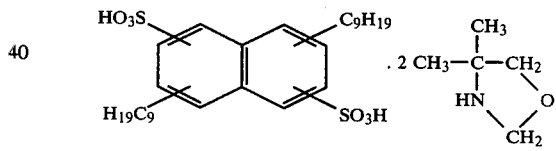

3. A composition as defined in claim 1 wherein said oxa-azacyclopentane is 4,4-dimethyl-1-oxa-3-aza-cyclopentane.

4. A composition as defined in claim 3 wherein said aromatic sulfonic acid is a polyalkylaromatic polysulfonic acid having a molecular weight of at least about 500.

5. A composition as defined in claim 3 wherein said aromatic sulfonic acid is a dinonylnaphthalene disulfonic acid, the nonyl radicals of which are highly branched.

6. A composition as defined in claim 3 wherein said aromatic sulfonic acid is a polyalkylaromatic sulfonic acid having a molecular weight of at least about 500.

7. A composition as defined in claim 3 wherein said aromatic sulfonic acid is a dinonylnaphthalene sulfonic acid.

8. A composition as defined in claim 3 wherein said aromatic sulfonic acid is an alkyl-benzene sulfonic acid.

9. A composition as defined in claim 3 wherein said aromatic sulfonic acid is para-toluene sulfonic acid.

* * * * *